United States Patent [19]

Wells

[11] Patent Number: 4,617,032
[45] Date of Patent: Oct. 14, 1986

[54] SAMPLE MODULATOR CELL FOR GAS CHROMATOGRAPHY

[75] Inventor: Gregory J. Wells, Suisun, Calif.

[73] Assignee: Varian Associates, Inc., Palo Alto, Calif.

[21] Appl. No.: 777,569

[22] Filed: Sep. 18, 1985

Related U.S. Application Data

[63] Continuation of Ser. No. 548,816, Nov. 4, 1983, abandoned.

[51] Int. Cl.⁴ .................... B01D 15/08; G01N 31/08
[52] U.S. Cl. ................................ 55/67; 55/197; 73/23.1; 436/161; 436/181
[58] Field of Search ............ 55/197, 386, 67; 73/23.1; 422/88, 89; 436/161, 174, 179–181

[56] References Cited

U.S. PATENT DOCUMENTS

| | | | |
|---|---|---|---|
| 2,451,882 | 10/1948 | Smith | 73/61 R |
| 3,357,232 | 12/1967 | Lauer | 73/23.1 X |
| 3,357,233 | 12/1967 | Roof | 73/23.1 |
| 3,740,154 | 6/1973 | Green | 356/187 |
| 3,811,253 | 5/1974 | Austin et al. | 55/73 X |
| 4,309,898 | 1/1982 | Horton | 73/23.1 |
| 4,316,381 | 2/1982 | Woodruff | 73/27 R |
| 4,316,382 | 2/1982 | Woodruff | 73/27 R |
| 4,442,217 | 4/1984 | Deans | 73/23.1 X |

Primary Examiner—Robert Spitzer
Attorney, Agent, or Firm—Stanley Z. Cole; David Schnapf

[57] ABSTRACT

A sample modulator cell for chromatographic analysis uses a diverting valve to send a carrier gas into a duct in a generally closed circular form periodically alternately through two separate ports. A sample inlet port opens between the carrier ports so that a sample-containing gas periodically alternately flows to an exit port through two channels A and B of different lengths in the duct. A phase-shift of 180° is introduced between the channels so that all of the sample introduced into the modulator will be used for the analysis, thus increasing the peak response.

18 Claims, 8 Drawing Figures

FIG. 3
(a) 
(b) 
(c) 
(d) 
(e) 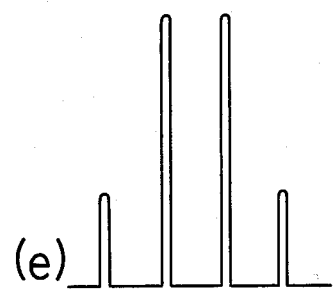
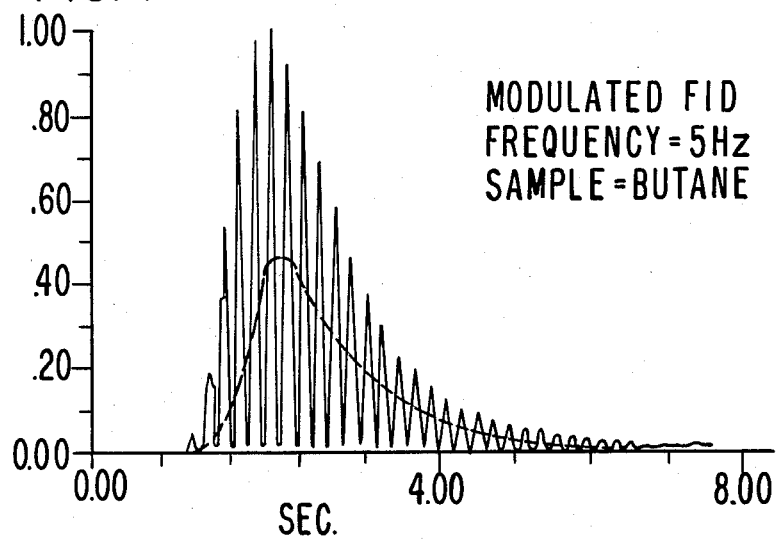
FIG. 4
MODULATED FID
FREQUENCY = 5Hz
SAMPLE = BUTANE

SAMPLE MODULATOR CELL FOR GAS CHROMATOGRAPHY

This application is a continuation of application Ser. No. 548,816, filed Nov. 4, 1983, now abandoned.

BACKGROUND OF THE INVENTION

This invention relates generally to a method of improving response in chromatographic analysis and more particularly to a sample modulator cell for synchronous detection with improved signal-to-noise ratio.

Two problems that limit the utility of detectors in gas chromatography are drift and noise. Examples of detectors that are subject to drift are the thermal conductivity detector (TDC) and the thermionic specific detector (TSD). The drift in the TCD is caused by small changes in the temperature of the cell wall. The drift in the TSD is caused by small changes occurring on the surface of the bead. These changes are both thermal and chemical. Examples of detectors in which the dominant noise source is within the detector cell are the flame photometric detector (FPD), flame ionization detector (FID) and the TSD. The noise in the FPD is caused by random low frequency fluctuations in the luminosity of the background flame. The TSD likewise suffers from fluctuations in the nature of the bead surface.

When the drift and noise sources are inherent to the detector and not to the electronics which controls the detector or amplifies the signal therefrom, it has been known to minimize or eliminate these problems by AC techniques. U.S. Pat. No. 3,740,154 issued to J. A. Green, for example, discloses a flame photometer whereby the gas to be analyzed is modulated in a modulator equipped with a flexible sinusoidally oscillating membrane. Since the sample gas comes into direct contact with this membrane, this modulator cannot be used for certain samples, such as caustic ones and those at a very high temperature. Fluid control systems not requiring a flexible membrane of the aforementioned type have been disclosed, for example, in U.S. Pat. No. 3,357,233 issued to L. B. Roof, and U.S. Pat. No. 4,309,898 issued to R. L. Horton, but both these devices are fluidic in nature and require a stream which is greater by orders of magnitude in order to properly operate.

U.S. Pats. Nos. 4,316,381 and 4,316,382 issued to T. A. Woodruff disclose a modulated detector which is provided with a storage volume for modulation in the fluid path so that the measurements are made only at times in which the flow has stopped. This is a static measurement, not a continuous dynamic process which allow shorter response times.

SUMMARY OF THE INVENTION

It is therefore an object of the present invention to provide a sample modulator for improving the signal-to-noise ratio of a chromatographic detector by synchronous detection.

It is another object of the present invention to provide a sample modulator with a means for alternately supplying a sample fluid into two inlets which means can operate effectively at flow rates substantially below those required for fluidic flow control systems.

It is still another object of the present invention to provide a sample modulator which allows continuous dynamic measurements.

It is a further object of the present invention to provide a sample modulator equipped with a valve means for alternately supplying a sample fluid into two inlets, said valve means not coming into direct contact with said sample fluid.

It is a still further object of the present invention to provide a sample modulator which allows all of the sample from a gas chramotographic column to be utilized in a detector.

BRIEF DESCRIPTION OF THE DRAWINGS

FIG. 3(a) is a sketch of the unmodulated profile of a chromatograph pulse.

FIG. 3(b) is sketch of the modulated profile as received through a first channel.

FIG. 3(c) is a sketch of the modulated profile as received through a second channel having 180° longer phase length.

FIG. 3(d) is a sketch of the modulated profile as received by combining both channels.

FIG. 3(e) is a sketch of the modulated profile as enhanced by a compression pulse.

FIG. 4 is a chromatogram obtained by a modulator cell of FIG. 2.

DETAILED DESCRIPTION OF THE INVENTION

Figure 1:
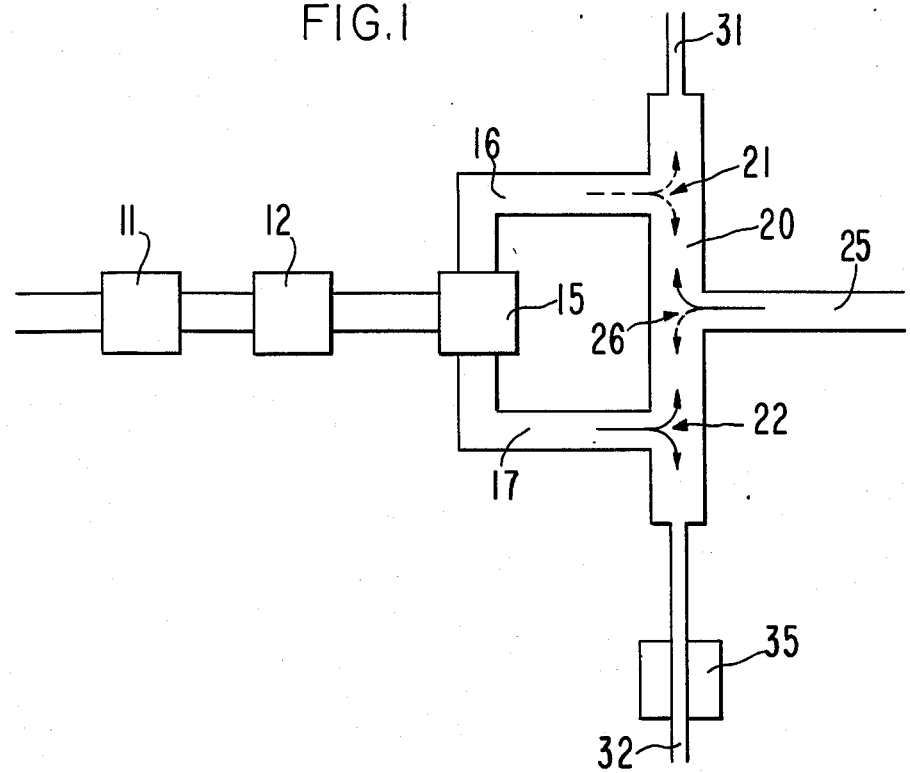
FIG. 1 shows schematically a sample modulator cell according to the present invention.

There is shown schematically in FIG. 1 the horizontal view of a sample modulator cell for a gas chromatographic detector embodying the present invention. A gas for controlling the direction of sample flow, which may hereinafter be referred as diverting gas, is flow-controlled by the combined action of a pressure regulator 11 and a flow restriction 12 of any known types and enters a diverting valve 15 which may be any mechanical device whose action is to alternately divert the incoming flow into an upper path 16 and a lower path 17. The upper and lower paths 16 and 17 open into a vertical duct 20 at points 21 and 22, respectively, the point 21 being above point 22. The sample to be analyzed enters the cell through an inlet 25 which opens into the duct 20, forming a tee 26 at a point between points 21 and 22. When the sample from the inlet 25 reaches the tee 26, it is alternately forced out of an upper vent 31 and a lower vent 32 by means of the gas diverting flowing through the lower path 17 and the upper path 16, respectively. In other words, during that phase of the alternate action of the diverting valve 15 when the diverting gas is diverted into the upper path 16, the sample from the inlet 25 is forced to flow downward inside the duct 20 and through the lower vent 32 as the gas movements are shown by the dotted arrows, while during the other phase of the alternate action of the diverting valve 15 when the carrier gas is diverted into the lower path 17, the sample from the inlet 25 is forced to flow upward inside the duct 20 and through the upper vent 31 as the gas movements are shown by the solid arrows. The duty cycle of the diverting valve 15 need not be evenly divided, nor is it necessary that a sample-containing gas should leave the upper vent 31 and the lower vent 32 respectively 50% of the time during each cycle. For high-frequency operations, it may be found advangtageous to reduce this ratio in view of the peak spreading.

In one mode of operation, the upper vent 31 may be connected, for example, to a fused silica detector insert of an indium-sensitized FPD (not shown). A balance load 35 on the lower vent 32 may be adjusted to equal the load downstream of the upper vent 31 due to the detector so that the net gas flow through each vent 31 and 32 will be the same and, secondarily, that a nearly constant flow of gas, either sample-containing or pure diverting gas, is always flowing through both vents 31 and 32 at all times of the operation. The modulated sample flow into the detector is converted to an electrical signal by a suitable transducer (not shown) and synchronously detected by any method known in the art.

Figure 2:
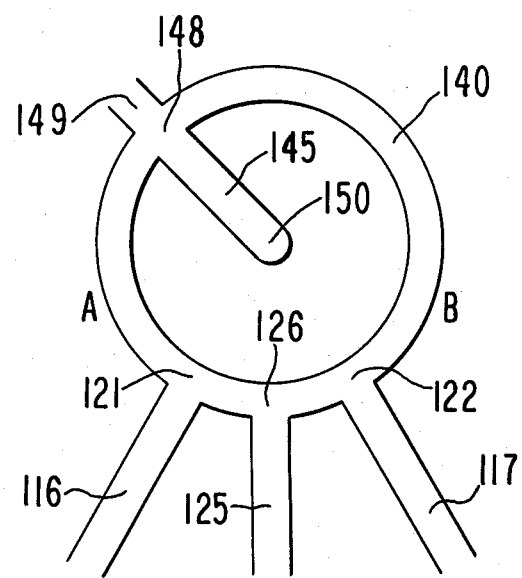
FIG. 2 shows another embodiment of sample modulator cell of the present invention.

Another mode of operating the modulator cell of the type shown in FIG. 1 is illustrated in FIG. 2. This mode is for remedying the disadvantage of the aforementioned operation wherein one-half of the sample leaving the gas chromatographic column is diverted away and not utilized in the detector. In order to utilize all of the sample and yet to achieve modulation so as to increase the peak response obtained by the modulator cell, the two passageways 116 and 117 from a diverting valve (not shown) and a sample inlet 125 open into a circular duct 140 at points 121, 122 and 126, respectively. An exit passageway 145 also opens into the circular duct 140 at point 148 and connects the latter to an exit port 150. For the convenience of explanation, the right- and left-hand parts of the duct 140 from the point 126 to point 148 moving clockwise and counter-clockwise will be called channels A and B, respectively. Point 148 is located so that channel B is twice as long as channel A. This is for the purpose of creating a 180-degree phase difference in the modulated sample flow through channels A and B as will be explained below.

In operating the modulator cell of FIG. 2, the diverting valve performs the same function as described above so that the carrier gas enters the duct 140 alternately at points 121 and 122. If a sample having a profile generally of the shape shown by Curve (a) of FIG. 3 is injected at 126 with a proper pressure, it will be alternately diverted into channels A and B by the motion of the carrier gas. The profiles of the modulated sample flow in channels A and B are shown by Curves (b) and (c) of FIG. 3 for a low frequency situation for the purpose of illustrating the mode of operation. As described above, the length of the channels A and B are such that there is introduced therein a phase difference of 180 degrees so that the sample mass flow measured at point 148 will be as shown by Curve (d) of FIG. 3 with peaks twice as high as those in either Curve (b) or (c). This desirable result is obtained because the half of the sample which leaves the cell through the lower vent (32 of FIG. 1) is not wasted, but is also utilized in the detector. Alternatively, if a periodic flow of gas such as a compression pulse of either controlled gas or fuel gas is applied through an entrance port 149 either at point 148 as shown in FIG. 2 or alternatively somewhere between points 148 and 150, the mass flow measured at point 150 will increase due to the increased gas flow. The phase of such compression pulse must of course be such that the sample portion of the wave form (FIG. 3(d)) is inside the exit passageway, or between points 148 and 150 when it is applied. For example, if the flow at point 148 is doubled when the compression pulse is applied, the same mass will pass through the exit port 150 in half the time so that the peak mass flow will have doubled and the flow profile will be as shown in FIG. 3(e). FIG. 4 shows the modulated sample profile for butane eluted from a capillary column at frequency of 5 Hz without the use of the aforementioned compression pulse through the entrance port 149. The dotted curve is the response from a FID to the modulated sample. The doubling in peak response obtained by the phase shifted modulator cell of FIG. 2 is illustrated.

The present invention has been disclosed above in terms of only a few examples, but they are intended to be illustrative rather than limiting, and the disclosure therefore should be broadly construed. For example, FIGS. 1 and 2 are merely schematic and do not represent dimensional relationships which are preferably. Thus, the duct 140 need not be exactly circular and the directions in which the passageways 116 and 117 and the inlet 125 open into the duct 140 need not necessarily be as depicted in FIG. 2. FIG. 1 need not necessarily be considered a horizontal view; the apparatus may be placed in any orientation with respect to the vertical in spite of the use above of expressions "upper", "lower" and "vertical". The diverting gas may, or may not be the same as the carrier gas used in gas chromatography. The scope of the present invention is limited only by the following claims.

What is claimed is:

1. A method of obtaining an improved response to noise ratio in a chromatographic analysis of a sample by means of a sample modulator, comprising the steps of:
   introducing said sample into a duct having two channels leading to a single exit passageway connected to a detector, periodically alternately introducing a carrier gas into said duct through two carrier gas inlets, said carrier gas inlets being positioned such that said sample gas is alternately directed to said two channels,
   said channels being of unequal length so that there is a phase shift of 180° at the frequency of said periodic alternations of said carrier gas flow in said two channels.

2. The method of claim 1 wherein all of said sample introduced into said duct by said sample-introducing step is utilized in said analysis by said detector.

3. The method of claim 1 wherein said phase-shift-introducing step comprises the step of adjusting the flow rate of said diverting gas into said duct.

4. The method of claim 1 further comprising the step of periodically applying an additional gas flow in said exit passageway in order to increase the peak response obtained by said modulator.

5. A sample modulator for gas chromatography comprising a duct forming a closed circuit, said duct comprising:
   two carrier gas input ports through which a carrier gas is introduced into said duct;
   a sample input port positioned between said carrier gas input ports, through which a sample gas is introduced into said duct;
   means for periodically switching a carrier gas input alternately between said carrier gas input ports;
   a single exit port positioned between said carrier gas input ports through which all the carrier gas and all the sample gas entering the duct exits the duct, said exit port being removed from said sample input port, thereby defining two channels connecting said sample input port and said exit port.

6. The modulator of claim 5 wherein said closed circuit duct is generally annular.

7. The modulator of claim 5 wherein said sample input port is equidistantly positioned between said carrier gas input ports.

8. The modulator of claim 5 wherein said switching means is adapted to cycle at a constant frequency and wherein each portion of said cycle is of substantially equal duration.

9. The modulator of claim 5 wherein said duct contains no moving parts.

10. The modulator of claim 5 wherein one of said two channels is longer than the other of said channels.

11. The modulator of claim 10 wherein said longer channel is about twice as long as said shorter channel.

12. The modulator of claim 5 further comprising an exit passageway connected to said duct, opening thereinto through said exit port.

13. The modulator of claim 5 further comprising a means for introducing an additional periodic gas flow in said exit passageway for increasing the measured sample mass flow at a downstream end of said exit passageway.

14. The modulator of claim 13 wherein said additional periodic gas flow is synchronized with said switching means.

15. A sample gas modulator for gas chromatography, comprising:
a duct formed as a continuous loop and having no moving parts,
a sample input port through which a continuous flow of sample gas is introduced into said duct,
a single exit port through which all the gas which enters said duct is channeled to a detector, said exit port and said sample input port defining first and second channels of unequal length in said duct, both of said channels connecting said sample input port and said exit port,
first and second carrier gas input ports spaced equidistantly about said sample input port through which a constant flow of carrier gas, greater in magnitude than the flow of said sample gas, is introduced into said duct, said first carrier gas input port being within said first duct channel and said second carrier gas input port being within said second duct channel,
means for periodically switching said constant flow of said carrier gas alternately between said carrier gas input ports, whereby when said carrier gas is introduced into said duct through said first carrier gas input port said sample gas is caused to travel through said second duct channel and when said carrier gas is introduced into said duct through said second carrier gas input port said sample gas is caused to travel through said first duct channel,
means for selecting the frequency of said switching means so that there is a phase shift of 180° between the sample gas moving through said first channel and the sample gas moving through said second duct channel at said exit port.

16. The sample modulator of claim 15 further comprising means for introducing an additional periodic flow in said exit port, the frequency of which is the same as the frequency of said switching means.

17. The sample modulator of claim 15 wherein said first channel is twice as long as said second channel.

18. The sample modulator of claim 15 wherein said duct is of generally annular shape.

* * * * *